United States Patent [19]

Quirk et al.

[11] Patent Number: 4,873,358
[45] Date of Patent: Oct. 10, 1989

[54] PREPARATION OF NITROESTERS VIA THE REACTION OF NITROPARAFFINS WITH CYANOFORMATES

[75] Inventors: Jennifer M. Quirk, Highland; Charles G. Carter, Silver Spring, both of Md.

[73] Assignee: W. R. Grace & Co.-Conn., New York, N.Y.

[21] Appl. No.: 246,609

[22] Filed: Sep. 20, 1988

[51] Int. Cl.$^4$ .............................................. C07C 79/41
[52] U.S. Cl. ...................................... 560/22; 560/20; 560/21; 560/156
[58] Field of Search ...................... 560/20, 21, 22, 156

[56] References Cited

U.S. PATENT DOCUMENTS

| | | | |
|---|---|---|---|
| 3,761,510 | 9/1973 | Sifniades | 560/156 |
| 4,433,162 | 2/1984 | Hamamoto et al. | 560/156 |
| 4,495,362 | 1/1985 | Honda et al. | 560/20 |

FOREIGN PATENT DOCUMENTS

| | | | |
|---|---|---|---|
| 56-145245 | 11/1981 | Japan | 560/156 |
| 57-149253 | 9/1982 | Japan | 560/156 |
| 2111494 | 7/1983 | United Kingdom | 560/156 |

OTHER PUBLICATIONS

Kornblum et al., J. Am. Chem. Soc., 77, 6654 (1955).
Finkseiner et al., J. Org. Chem., 28, 215 (1963).
Zen et al., J. Chem. Soc. of Japan, Ind. Chem. Sec., 74, 70 (1971).
Sifniades, J. Org. Chem., 40, 3562 (1975).
Angew. Chem. Int. 21 139 No. 2 (1982).

*Primary Examiner*—Bruce Gray
*Attorney, Agent, or Firm*—Howard J. Troffkin

[57] ABSTRACT

A process to form alkyl nitroacetates by reacting, in a common solvent and in the presence of a base, a nitroparaffin and a cyanoformate. The desired product is formed by a simple one-step process using inexpensive and readily available reactants.

19 Claims, No Drawings

PREPARATION OF NITROESTERS VIA THE REACTION OF NITROPARAFFINS WITH CYANOFORMATES

BACKGROUND OF THE INVENTION

The present invention relates to a commercially feasible process for preparing alkyl nitroacetates. More particularly, it relates to a process for preparing alkyl nitroacetates by reacting a nitroparaffin with a cyanoformate in the liquid phase.

Alkyl nitroacetates are useful compounds for preparing alpha-nitrocarboxylic acids by reacting the same with alkyl halide, aldehyde, tertiary amines, and the like. It is also well known that production of amino acids such as phenyl alanine, dopa, methyl dopa, tryptophan, alpha-methyltryptophan, etc. is easily carried out by hydrogenating alpha-nitrocarboxylic acids.

Various processes for preparing alkyl nitroacetates are known. For example, (1) Kornblum et al. reported in J. Am. Chem. Soc., 77, 6654 (1955) that ethyl nitroacetates were obtained by reacting ethyl iodoacetate with silver nitrite; (2) Kinkseiner and his coworkers reported in J. Org. Chem., 28, 215 (1963) that a magnesium complex of nitroacetic acid was obtained by reacting nitromethane with methyl carbonate magnesium, which was, then subjected to esterification to obtain nitroacetic acid ester using a strong acid; (3) Zen et al. reported in J. Chem. Soc. of Japan, Ind. Chem. Sec., 74, 70 (1971) that methazonic acid salt was obtained by reacting 2 moles of nitromethane with 8 moles of potassium hydroxide, which was then esterified to obtain a nitroacetic acid ester using a strong acid; (4) Sifniades and others disclosed in J. Org. Chem., 40, 3562 (1975) that a nitroacetoacetic acid ester was obtained by reacting an acetoacetic acid ester with an acyl nitrate, which was then decomposed with an alcohol to obtain a nitroacetic acid ester and (5) Honda et al., in U.S. Pat. No. 4,495,362, disclose that alkyl nitroacetates can be formed by reacting a nitroparaffin with an alkyl phenyl carbonate.

Among the processes mentioned above, processes (1) and (2) are not practical as they involve the use of expensive silver salt or magnesium metal as starting materials. Process (3) is not feasible on a large scale application as the reaction requires heating of alkali metal salts of nitromethane which presents the possibility of a dangerous detonation. Process (4) necessitates the use of relatively expensive materials, such as acetoacetic acid ester and acyl nitrates while process (5) requires the use of alkyl phenyl carbonate, a material which is not commercially available, is formed from phosgene and, thereby, presents a handling and safety problem and which, when formed, requires a difficult separation from the product mixture which includes the dialkyl and diphenyl derivatives as well.

SUMMARY OF THE INVENTION

An object of the present invention is to provide a process for preparing alkyl nitroacetates from a nitroparaffin and a cyanoformate utilizing readily available and inexpensive reactants to provide a commercially feasible process.

Another object of the present invention is to provide a process for preparing alkyl nitroacetate in which the reaction can be completed even at room temperature.

The present invention is directed to a simple, one step, commercially feasible process for forming alkyl nitroacetates using readily available and inexpensive reactants. The process comprises reacting, in a suitable solvent and in the presence of a base, a nitroparaffin and a cyanoformate.

DETAILED DESCRIPTION OF THE INVENTION

Nitroparaffins used as the starting material in the present invention include compounds represented by the formula (I):

wherein $R_1$ and $R_2$ are hydrogen atom, an unsubstituted or substituted alkyl group having 1 to 7 carbon atoms, or an unsubstituted or substituted phenyl group. The substitution can be a halo, nitro alkyl or aryl group. They are, for example, nitromethane, nitroethane, 1-nitropropane, 2-nitropropane, 1-nitrobutane, 2-nitrobutane, 1-nitroisobutane, 1-nitrooctane, 2-phenylnitroethane, p-chlorophenyl nitromethane, p-nitrophenyl nitromethane, and the like. Preferably, compound I is a primary nitroalkane and most preferably a $C_1$-$C_3$ nitroalkane.

The cyanoformates suitable for use in the present invention can be represented by the formula (II):

wherein $R_3$ represents an unsubstituted or substituted lower alkyl group, preferably a $C_1$-$C_4$ alkyl. Examples of compound II include methyl cyanoformate, ethyl cyanoformate and the like. These compounds are readily available in industrial quantities and are readily prepared from the industrially available chloroformates.

The molar ratio of reactants I and II to be used in the present process as starting material can range from about 1:05 to 1:10 and preferably between 1:1 and 1:3. The overall reaction is most preferably conducted by using a 1:1 molar ratio of reactants I and II. Although less or greater amounts can be used, it is most effective to use the ratios disclosed above. When large excesses of II are used, the process is most effective by recovering and recycling the unreacted cyanoformate.

The subject process is a single step reaction to provide a desired, valuable material from readily attainable and inexpensive starting reactants. The overall reaction is:

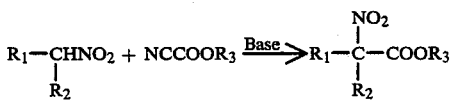

The three components (nitroparaffin, base and cyanoformate) can be introduced into a common solvent, as described below, in any order. For example, the nitroparaffin and cyanoformate can be first introduced into a solvent and subsequently introduce the base. Alternately, the base and nitroparaffin are introduced in any order into the reaction solvent and then the cyanoformate is introduced into the reaction zone. Details of preferred modes of causing the subject process to be conducted are described hereinbelow.

The reaction requires the presence of a base. It is believed, although not to be a limitation on the present invention, that the base provides a means for removing a proton from the alpha carbon and forming the reactive carbanion specie. The base can be any strong base selected from any hydride, hydroxide, alkoxide or oxide. Examples are any alkali or alkaline earth metal (preferably sodium or potassium) base such as the hydrides, hydroxides, or alkoxides of these metals, oxides of alkaline earth metals, such as calcium oxide and the like, substituted ammonium hydroxides wherein the substituted group is each independently selected from an alkyl or aralkyl group, such as methyl, ethyl, butyl, benzyl and the like or a substituted phosphonium hydroxide where the substituted group is each independently selected from an alkyl, aryl or aralkyl group such as methyl, ethyl, butyl, phenyl, benzyl and the like. The base and the nitroparaffin are normally charged into the reaction zone in a molar ratio of from about 0.8 to 1.2 (preferably about 1:1).

One mode of carrying out the subject synthesis comprises contacting a base, as described above, with a nitroparaffin solution. The nitroparaffin-base adduct is normally only slightly soluble and, thereby, when present in large quantities, forms a slurry to which the cyanoformate is incrementally added. The disappearance of the slurry provides an indication of completion of the reaction with the desired product (in the form of its salt) dissolved in the reaction medium. The cyanoformate readily reacts with the nitroparaffin-base adduct to provide this desired product. It is, therefore, unnecessary to conduct the synthesis by this mode at elevated temperatures. It is preferable to run the reaction under low temperatures, such as below 40° C. and most preferably at ambient temperatures.

Alternately, the subject synthesis can be carried out by introducing the nitroparaffin and the cyanoformate into a common solvent and then incrementally introducing a base. The cyanoformate will not actively react with the nitroparaffin, per se. As the base is introduced it will generate the nitroparaffin-base adduct in small amounts which will, in turn, react with the cyanoformate in a short period.

In each of the above described modes, the synthesis is preferably carried out using an alkali or alkaline earth metal hydride as the base to avoid a build-up of large amounts of water or alkanol by-product in the system. Hydroxide and alkoxide bases may be used if the reaction solvent is substantially immiscible to water or if other conventional means (e.g., molecular sieve, anhydrous salts of magnesium sulfate, sodium sulfate, calcium sulfate and the like) are used to remove the by-product material.

An alternate preferred mode of carrying out the present reaction is to add to a solution of nitroparrafin, small, incremental quantities of base (hydride, hydroxide or alkoxide) and then to add substantially the same molar amount with respect to the base of the cyanoformate. Alternately, incremental amounts of nitroparaffin, base and cyanoformate can be added to a reaction media solvent. These incremental additions can be cyclically repeated to provide a solution of desired product in good yields. This process is preferred when the base is an alkoxide or hydroxide and no means for removing the by-product water or alkanol is used. This mode provides a continuous process in which the product can be removed incrementally at the end of any one cycle. This process mode also provides a means of maintaining all of the reactants and products in solution and thus has the advantage of alleviating problems associated with a two phase (slurry) reaction.

In addition to the above described required reactants, the reaction media can contain a phase transfer agent to further enhance the rate of the reaction. Any known phase transfer agent can be used as is well known to the artisan which include, for example, cyclic ethers, such as 18-crown-6, 15-crown-5 and the like (the first number indicates total atoms while the second number indicates oxygen atoms present in the cyclic ether), tetraalkylammonium salts such as tetramethylammonium chloride, and the like as well as tetraalkyl phosphonium and tetraaryl phosphonium salts, such as tetrabutyl phosphonium chloride, tetraphenyl phosphonium chloride and the like.

The present invention should be conducted in the liquid phase. The reactants should be at least partially soluble in a common solvent. Any liquid capable of dissolving all or at least a portion of reactants I and II and base can be used. Such solvents may or may not be polar and include hydrocarbons such as hexane, cyclohexane, benzene, toluene and the like, as well as nitriles such as acetonitrile and the like, ethers, such as tetrahydrofuran, dioxane and the like, amides such as dimethylformamide, dimethylacetamide, N-methylpyrrolidone, and the like, sulfur compounds such as dimethylsufoxide, sulfolane, and the like, and alkylated cyclic ureas such as N,N'-dimethyl ethyleneurea, N,N'-dimethyl propyleneurea and the like.

There is no specific limit to the amount of the solvent. The amount is suitably selected depending on the starting materials, the reaction conditions, and the type of solvents used. The solvent is normally used in amounts of up to about ten times the weight of the starting materials.

The reaction pressure may be reduced, ambient, or elevated. The reaction temperature can be in the range of from about $-20°$ C. to 150° C., and more preferably between about 0° C. and 100° C. and most preferably between about 10° C. and 40° C. Although the reaction time varies depending on the temperature, the type of solvent, etc., it is usually in the range of 10 minutes to 20 hours. In most instances the reaction is preferably carried out at ambient temperature and pressure conditions and is completed within a short period of less than about one hour.

The desired product can be obtained by various conventional means such as extracting, separating, drying and distillation. For example, the resultant solution of the reaction can be made acidic and the salt by-product extracted with water leaving a solution which contains the desired alkyl nitroacetate. The product can either be extracted or distilled at reduced pressure while maintaining an acidic pH (such as below 6).

The following examples are given for illustrative purposes only and are not meant to be a limitation on the invention as defined by the claims, appended hereto. All parts are by weight unless indicated otherwise.

EXAMPLE 1

To a 100 ml 3-neck round bottom flask equipped with an additional funnel, thermometer and condenser topped with an $N_2$ inlet was added 20 ml tetrahydrofuran (THF) and 0.19 g (0.008 mole) sodium hydride. To this was added dropwise 0.5 g (0.008 mole) nitromethane. The reaction was then stirred at room temperature for 15 minutes during which time a slurry formed. 0.8 g (0.009 mole) ethyl cyanoformate was added dropwise. The mixture was a homogeneous solution at the conclusion of this addition. The reaction was stirred at room temperature for 18 hours after which time it was acidified to pH 4–5 with 1 N HCl. The yield of ethyl nitroacetate was determined to be 77% by gas chromatography.

EXAMPLE 2

The reaction was run as described in Example 1 except that nitroethane was used instead of nitromethane. The yield of ethyl nitropropionate was 65%.

EXAMPLE 3

The reaction was conducted as described in Example 1 except that 2-nitropropane was used instead of nitromethane. The yield of nitroester was 59%.

EXAMPLE 4

The reaction was conducted as described in Example 1 except that hexane was used as solvent instead of THF. The yield of ethyl nitroacetate was 71%.

EXAMPLE 5

The reaction was conducted as described in Example 1 above except that benzene was used as solvent instead of THF. The yield of ethyl nitroacetate was 87%.

EXAMPLE 6

For comparative purposes, the reaction was conducted as described in Example 1 above except that an amine base, triethylamine, was used instead of sodium hydride. Analysis of the resultant reaction mixture by gas chromatography showed that no ethyl nitroacetate was formed.

EXAMPLE 7

To a 100 ml three-neck round bottom flask, equipped with an addition funnel, a thermometer and a condenser topped with a nitrogen gas inlet tube, was added 20 ml of dimethylsulfoxide, 0.196 g (0.00815 mole) sodium hydride and then 0.5 g (0.00815 mole) of nitromethane was added dropwise at ambient temperature to give a slurry. 1.6 ml (0.0163 mole) of ethyl cyanoformate was then added dropwise forming a homogeneous solution and was then stirred for 2 hours at ambient temperature. The solution was made acidic by adding 30 ml of 1 Normal acetic acid with stirring. The product was extracted with ethyl acetate and dried over magnesium sulfate. Ethyl nitroacetate was formed in 83% yield as determined by gas chromatography.

EXAMPLE 8

The reaction was conducted as described in Example 7 above except that tetramethylammonium hydroxide was used instead of sodium hydride. The yield of ethyl nitroacetate was 23%.

EXAMPLE 9

To a 100 ml three necked round bottom flask, equipped with a liquid addition funnel, a solid addition funnel and a condenser topped with a nitrogen inlet, was added 20 ml of dimethylsulfoxide and 1.08 g (0.0178 mole) nitromethane. 0.1 g (0.00178 mole) potassium hydroxide followed by 1 ml of a 20% solution of ethyl cyanoformate in (0.0021 mle) dimethylsulfoxide. The solution was stirred for a short period and the addition of each reactant (base and formate) was repeated nine times. The resultant solution remained homogeneous throughout the addition process, was stirred at ambient temperature for one hour and then acidified to pH of 4 with conc. hydrochloric acid. The product was extracted with ethyl acetate and dried with anhydrous magnesium sulfate. The magnesium sulfate was filtered off and solvent evaporated to give ethyl nitroacetate in 68% yield.

What is claimed:

1. A process for forming an alkyl nitroacetate represented by the formula:

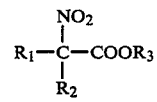

wherein $R_1$ and $R_2$ each independently represent a hydrogen atom, an unsubstituted or substituted $C_1$–$C_7$ alkyl group or an unsubstituted or substituted phenyl group and $R_3$ is a $C_1$–$C_4$ alkyl group, comprising contacting in a liquid, a strong base, a nitroparaffin of the formula:

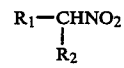

wherein $R_1$ and $R_2$ are the same as defined above, with a cyanoformate of the formula:

wherein $R_3$ is the same as defined above, an recovering the formed alkyl nitroacetate.

2. The process in claim 1 wherein said nitroparaffin is selected from nitromethane, nitroethane, 1-nitropropane, 2-nitropropane, 1-nitrobutane, 2-nitrobutane, 1-nitroisobutane, 1-nitrooctane, 2-phenyl nitroethane, p-chlorophenyl nitromethane or p-nitrophenyl nitromethane.

3. The process of claim 1 wherein the base is a hydride, hydroxide, alkoxide or oxide compound.

4. The process of claim 3 wherein the base is selected from a hydride, hydroxide or alkoxide of an alkali or alkaline earth metal, an oxide of an alkaline earth metal, an alkyl or aralkyl substituted ammonium hydroxide or an alkyl, aryl or aralkyl substituted phosphonium hydroxide.

5. The process of claim 3 wherein the base is selected from an alkali or alkaline earth metal hydride.

6. The process of claim 4 wherein the base is selected from a hydroxide or alkoxide and the liquid media is substantially immiscible to water or is in contact with a means for removing formed water or alkanol.

7. The process of claim 1 wherein said nitroparaffin, base and cyanoformate are contacted in the presence of a common solvent.

8. The process of claim 3, 4, 5 or 6 wherein said nitroparaffin is selected from a $C_1$–$C_3$ nitroalkane.

9. The process of claim 4 or 6 wherein the base and nitroparaffin are initially contacted in the liquid media and the cyanoformate is subsequently added thereto.

10. The process of claim 3, 4, 5 or 6 wherein the nitroparaffin and cyanoformate are initially contacted in the liquid media and the base is subsequently added thereto.

11. The process of claim 1 wherein (a) the base and nitroparaffin are contacted in a liquid media to provide a nitroparaffin-base adduct in an amount which is substantially soluble in the reaction liquid, (b) then introducing a substantially equal molar amount of cyanoformate to said liquid with respect to the molar amount of base used in (a), and (c) repeating (a) and (b) to provide the desired amount of nitroester product.

12. The process of claim 1 wherein the cyanoformate is a compound such that $R_3$ is selected from methyl, ethyl or propyl.

13. The process of claim 1 wherein the molar ratio of said nitroparaffin to said cyanoformate is in the range of 1:0.5 to 1:10.

14. The process as claimed in claim 13 wherein the molar ratio of said nitroparaffin to said cyanoformate is in the range of 1:1 to 1:3.

15. The process as claimed in claim 1 wherein said solvent is selected from acetonitrile, tetrahydrofuran, dioxane, dimethylformamide, dimethylacetamide, dimethyl sulfoxide, sulfolane, N-methylpyrrolidone, N,N'-dialkyl ethyleneurea or N,N'-dialkyl propyleneurea.

16. The process as claimed in claim 1 wherein the reaction is conducted at a temperature within the range of about $-20°$ to $150°$ C.

17. The process as claimed in claim 3 wherein the reaction is conducted at a temperature within the range of about $10°$ to $40°$ C.

18. The process of claim 1 or 9 wherein the reactants are contacted in the presence of a phase transfer agent.

19. The process of claim 18 wherein said agent is selected from a crown ether, a tetraalkyl ammonium halide, a tetraaryl phosphonium halide or a tetraalkyl phosphonium halide.

* * * * *